Figure 1:
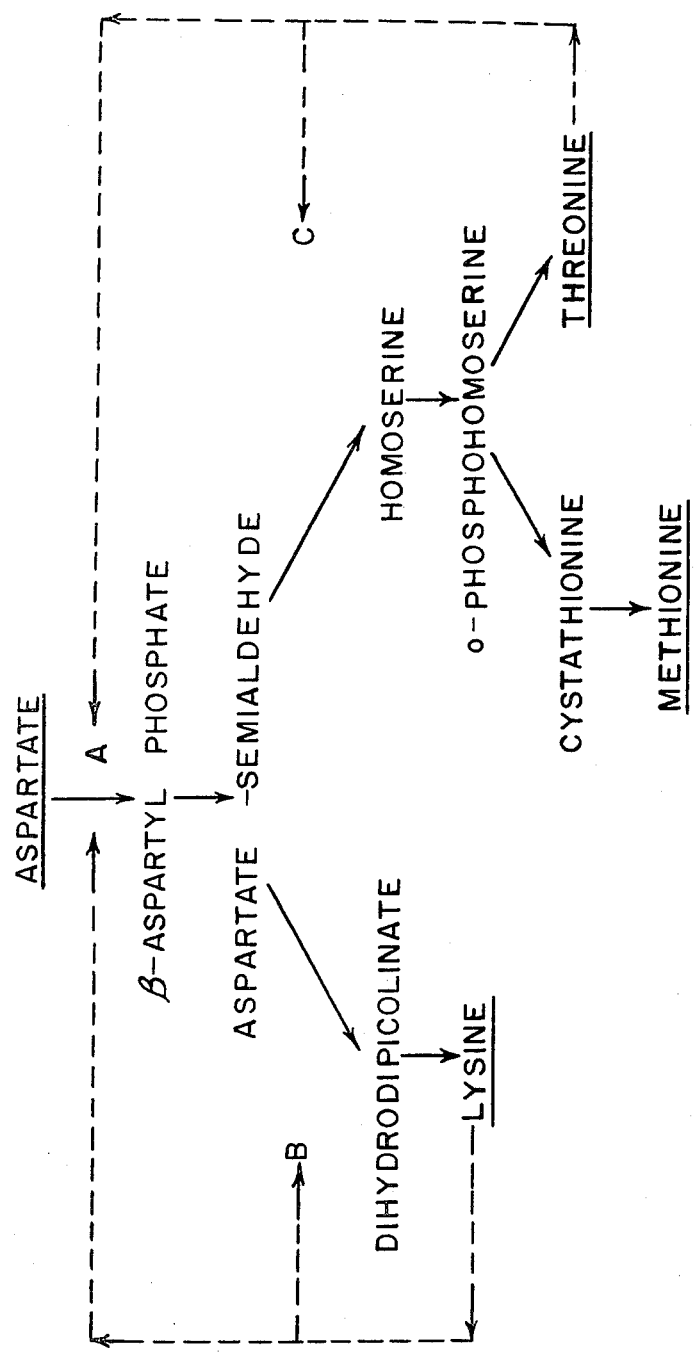

United States Patent [19]

Henke

[11] 4,425,737

[45] Jan. 17, 1984

[54] METHODS FOR MUTANT SELECTION IN CEREAL CROPS

[75] Inventor: Randolph R. Henke, Knoxville, Tenn.

[73] Assignee: Agrigenetics Research Associates Limited, Boulder, Colo.

[21] Appl. No.: 311,405

[22] Filed: Oct. 14, 1981

[51] Int. Cl.³ ............................................. A01G 1/00
[52] U.S. Cl. .................................. 47/58; 47/DIG. 1
[58] Field of Search ........................ 47/58, DIG. 1, 1

[56] References Cited

PUBLICATIONS

Cuvellier, G., et al., (1979), "A Method for Automatic Alpha-Amylase Measurement Applicable to Barley Genetics and to Malting and Brewing", Brewers Digest, Mar. 1979, pp. 42 and 43.

Eswaran, S., et al., "Methods for the Screening of Amylase-Producing Mutants in Aspergillus niger", Journal of Applied Bacteriology, vol. 45, 1978, pp. 287-289.

Fossum, K. et al., (1974), "Simple Method for Detecting Amylase Inhibitors In Biological Materials", Journal of Nutrition, vol. 104, pp. 930-936.

Hibberd, K. A., et al., (1980), "Selection and Characterization of a Feedback-Insensitive Tissue Culture of Maize", Planta, 148, pp. 183-187.

Radin, D. N. et al., (1978), "Herbicide-Tolerant Tobacco Mutants Selected in situ and Recovered via Regeneration from Cell Culture", Genetic Research Comb., vol. 32, pp. 85-89.

Singh, M., et al., "Inhibition of Corn, Soybean and Wheat Seedling Growth by Amino Acid Analogs", Cropscience, vol. 15, pp. 79-81.

Maliga, P., (1980), "Isolation, Characterization, and Utilization of Mutant Cell Lines in Higher Plants", International Review of Cytology, Supplement 11A, pp. 225-250.

Ho, T. D., et al., (1980), "Screening for Barley Mutants with Altered Hormone Sensitivity in their Aleurone Layers", Plant Physiology, vol. 66, pp. 153-157.

Heigaard, J., et al., (1979), "Brief Reports: B-Amylase Activity—A Simple Screening Test in Hiproly Barley Breeding", Hereditas, vol. 90, pp. 145-147.

Ho, T. D., (1979), "Hormonal and Genetic Regulation of Alpha-Amylase Synthesis in Barley Aleurone Cells", Genome Organization and Expression in Plants, Leaver, C. J. (Ed) Plenum Press, New York, pp. 147-157.

Campbell, J. A., (1980), "Measurement of Alpha-Amylase in Grains", Cereal Foods World, vol. 24, No. 2, pp. 46-49.

Hejgaard, J. et al., (1979), "Screening for Alpha-Amylase in Cereals Improved Gel-Diffusion Assay Using a Dye-Labelled Starch Substitute", Carlsberg Research Communication, vol. 44, pp. 21-25.

Henke, R. R., (1980), (Oral Presentation), "Selection of Biochemical Mutants in Plant Cell Given at Propagation of Higher Plants through Tissue Culture: Emerging Cultures "Technologies and Strategies", Univ. of Tenn., Dept. of Botany.

Henke, R. R., et al., (1979), "A Possible Screen for Detecting Increases in the Level of Soluble Lysine in Barley Endosperm", 1979 Annual Meeting of the American Society of Plant Physiologists, vol. 63.

Bright, S. W. J. et al., (1979), "Isolation of a Recessive Barley Mutant Resistant to S-(2-Aminoethyl)-cysteine", Theor. Appl. Genet., vol. 55, pp. 1-4.

Henke, R. R., et al., "Selection of Diverse Types of Biochemical Mutants Expressed in Barley Seeds", Presented to IV International Barley Genetics Symposium, Edinburough, Scotland, Jul. 1981.

Primary Examiner—James R. Feyrer
Attorney, Agent, or Firm—Pennie & Edmonds

[57] ABSTRACT

A method is disclosed which selects for different types of mutants expressed in cereal seed. The method allows rapid qualitative or quantitative screening of the aleurone $GA_3$-induced expression of alpha-amylase activity in half-seeds (without embryo). Half-seeds of the $M_2$ population of mutagenized cereal seeds are incubated under selection pressures that normally inhibit the expression of alpha-amylase activity. These selection agents include metabolic inhibitors which may function at the level of transcription, translation, or protein secretion.

These selection agents include antimetabolites such as amino acid analogs (e.g., S-2-aminoethylcysteine, p-flourophenylalaine, canavanine, etc.), antibiotics (e.g. Actinomycin D, cycloheximide, erythromycin, kanamycin, streptomycin, or tunicamycin), biocides, herbicides, water or salt stress. Such selection pressures may be applied to the half-seed method in the presence of absence of $GA_3$, ABA, and at various incubation temperatures. Once the half-seeds which produce alpha-amylase in the presence of the selected antimetabolite are identified, the corresponding embryo-containing portion of the seed may be germinated and grown to maturity.

25 Claims, 1 Drawing Figure

A = β-aspartate kinase
B = Dihydrodipicolinate synthase
C = Homoserine dehydrogenase

METHODS FOR MUTANT SELECTION IN CEREAL CROPS

TABLE OF CONTENTS

1. Introduction
2. Background of the Invention
   2.1 Selection of Mutants: Some Considerations and Problems
      2.1.1 Genetic and Epigenetic Variation
      2.1.2 Criteria for Identifying a Mutant
      2.1.3 Alternative Approach for Identifying a Mutant
   2.2 Barley Aleurone Physiology
      2.2.1 The Role of Gibberellic Acid
      2.2.2 RNA Metabolism
      2.2.3 Alpha-amylase Secretion in Barley Aleurone
      2.2.4 Abscisic Acid Effects on Aleurone Physiology
   2.3 Alpha-amylase Genetics
   2.4 Selection for High Free Lysine Mutants
   2.5 Use of Bioactive Agents as Selection Pressures
   2.6 Alpha-amylase Assays
3. Summary of the Invention
   3.1 Brief Description of the Invention
   3.2 General Approach and Rationale
4. Brief Description of the Drawing
5. Alpha-amylase Half-seed Screen: Protocol
6. Advantages of the Invention
7. Examples
   7.1 Mutagenesis
   7.2 Standard $M_2$ Screening Conditions
   7.3 Selective Agents Used

1. INTRODUCTION

This invention relates to a process for the selection of different types of mutants that may occur or be generated in barley, wheat, and other cereal crops. The method of the invention allows for rapid qualitative or quantitative screening of the aleurone gibberellic acid-induced expression of alpha-amylase activity under different selection pressures in half-seeds (i.e., seeds from which the embryo has been removed). Mutagenized $M_2$ seed populations (second generation seeds of the mutagenized population) are screened for alpha-amylase activity under selection conditions that normally inhibit the expression of alpha-amylase; such selective agents may inhibit or interfere with, for example, DNA transcription, messenger RNA (mRNA) translation, activity of the protein or secretion of the protein. Mutants are selected that synthesize and release alpha-amylase under such selection pressures.

This mutation selection methodology allows for the isolation of different types of biochemical mutants of nuclear and cytoplasmic origin. Such mutants would contribute significantly as a source of markers for use in genetic studies, as experimental probes to aid investigations in plant metabolism and regulation, and, most significantly, as a source of new germplasm for crop improvement.

Mutation selection methodologies that can conveniently and reproducibly isolate diverse types of mutants are not presently available in higher plants. The selection protocol of the present invention satisfies the important need for such a method.

2. BACKGROUND OF THE INVENTION

2.1 Selection of Mutants: Some Considerations and Problems

2.1.1 Genetic and Epigenetic Variation

Mutation is commonly defined as a permanent, heritable change in the primary structure of the genetic material, DNA. Some variations in the operational definitions relating to specific alterations in the genetic material that are included in the definition of mutation can be found in the literature. For example, Siminovitch (1976, Cell 7: 1-11) defines mutation as including point mutations, deletions, and chromosomal rearrangement (e.g., inversions and translocations), as well as aneuploidy. Maliga (1976, Isolation of mutants from cultured plant cells. Pages 59-76 in D. Dudits, G. L. Farkas and P. Maliga, eds. Cell Genetics in Higher Plants) excludes aneuploidy and polyploidy from the definition of mutation. For purposes of the present invention the term "mutation" is understood to include point mutations, deletions, chromosomal rearrangement, aneuploidy and polyploidy.

A change in the primary structure of DNA may result in an altered phenotype that may be recognized with varying degrees of facility, depending upon the specific nature of the selection pressure employed as well as the nature of the genetic change. Numerous kinds of altered phenotypes have been detected in plant cells in culture. However, a mutational event may not have been the basis for the altered phenotype observed in each of these cells. Generally, alterations in phenotypic expression that are not due to a mutational event are classified as epigenetic variations. Such changes may result, for example, from the ability of a cell line to alter the expression of its genes in response to a selective pressure (Binns, 1981, Developmental variability in plant tissue culture. In M. J. Constantin, R. R. Henke, K. W. Hughes and B. V. Conger, eds. Propagation of Higher Plants Through Tissue Culture: Emerging Technologies and Strategies. Environmental and Experimental Botany, Pergamon Press Ltd.). When direct and complete genetic analysis is not possible, phenotype changes arising in somatic cells as a result of epigenetic events may be difficult to distinguish from those resulting from mutational events (Melchers, 1971, Les Cultures de Tissue de Plantes. Colloq. Int. C.N.R.S., 193: 229-234). A feature common to all apparent epigenetic variations is the inability of these cell lines to maintain the altered phenotype in the absence of the selective pressure. Examples of epigenetic variation include cytokinin habituation of crown gall tumor cells (Meins and Binns, 1977, Proc. Natl. Acad. Sci. U.S.A. 74: 2928-2932), gradual increase in urease activity in tobacco XD cells (Skokut and Filner, 1980, Plant Physiol. 65: 995-1003), auxin habituation (Melchers, 1971, Les Cultures de Tissue de Plantes. Coloq. Int. C.N.R.S., 193: 229-234), transient cycloheximide resistance (Maliga et al., 1973, Nature New Biol. 244: 29-30), and colchicine-induced resistance to streptomycin and N-methyl-alanine (Zryd, 1979, Experimentia 35: 1168-1169).

2.1.2 Criteria for Identifying a Mutant

It is apparent, then, that simply applying a selective pressure to untreated or mutagenized cell cultures or whole plants and recovering individuals exhibiting the variant phenotype may not result in the isolation of a mutant. Care must be taken to use the appropriate criteria for classifying the altered phenotype as mutant. The following four criteria have been used to form the basis for this classification: (a) the variant phenotype should remain stable through consecutive generations; (b) the variant phenotype should arise spontaneously at low frequencies which may be enhanced with mutagens; (c) the variant phenotype should be correlated to altered gene products; or the most direct method, (d) the variant phenotypes should be transmitted in sexual crosses.

2.1.3 Alternative Approach for Identifying a Mutant

Mutation selection methodologies in bacteria and yeast have provided scientists with a wide variety of mutants that have contributed significantly to the elucidation of the biochemical reactions in, and the genetic basis for, cellular metabolism. In contrast, the ability to select for specific types of mutants in higher plants is far less developed. Factors contributing to this lack of success include (a) a poor understanding of the physiological basis of the selection pressures employed, and (b) difficulty in developing selection methodologies capable of screening the necessary number of individuals expediently. During the last decade several examples of variant cell lines that have resulted from mutation (i.e., where the above-noted criteria have been met) have been reported (Table 1). Many other variant cell lines will probably be proven mutants as well; however, even with the application of new plant cell and tissue culture technologies, progress has been slower than originally had been anticipated.

TABLE 1
MUTATIONS DERIVED THROUGH CELL CULTURES

| Plant Species | Variant Phenotype | Inheritance Pattern | Ref.* |
|---|---|---|---|
| Nicotiana tabacum | Methionine sulfoximine-resistant | Semidominant, two recessive loci with additive effects | 1 |
| Nicotiana tabacum | Streptomycin resistant | Uniparental | 2 |
| Nicotiana tabacum | 5-bromodeoxyuridine resistant | Semidominant | 3 |
| Nicotiana tabacum | Valine resistant | Dominant, Semidominant | 4 |
| Nicotiana tabacum | Chlorate resistant (nitrate reductase deficient) | Recessive (complementation via protoplast fusion) | 5; 6 |
| Nicotiana tabacum | Glycerol utilizing | (trait passed through crosses) | 7 |
| Nicotiana tabacum | Herbicide (picloram) resistant | Dominant and Semidominant | 8; 9 |
| Nicotiana tabacum | Carboxin resistant Dominant | 10 | |
| Nicotiana tabacum | Isonicotinic acid hydrazide resistant | Dominant | 11 |
| Zea mays | Helminthosporium toxin resistant | Maternal | 12 |
| Zea mays | Lysine and threonine resistant | Dominant | 13 |
| Oryza sative | 2-aminoethyl-cysteine | Dominant | 14 |

References:
1 Carlson, 1973, Science 180: 1366–1368.
2 Maliga et al., 1973, Nature (New Biol.) 244: 29–30.
3 Marton and Maliga, 1975, Plant Sci. Lett. 5: 77–81.
4 Bourgin, 1978, Molec. Gen. Genet. 161: 225–230.
5 Muller and Grafe, 1978, Molec. Gen. Genet. 161: 67–76
6 Glimelius et al., 1978, Physiol. Plant Pathol. 44: 273–277.
7 Chaleff and Parsons, 1978, Genetics 89: 723–728.
8 Chaleff, 1980, Theor. Appl. Genet. 58:91–95.
9 Chaleff and Parsons, 1978, Proc. Natl. Acad. Sci. U.S.A. 75: 5104–5107.
10 Polacco and Polacco, 1977, Ann. N.Y Acad. Sci. 287: 385–400.
11 Berlyn, 1980, Thero. Appl. Genet. 58: 19–26.
12 Gengenbach et al., 1978, Proc. Natl. Acad. Sci. U.S.A. 74: 5113–5117.
13 Hibberd and Green (personal communication).
14 Schaeffer, 1981, Mutations and selections: Increased protein from regenerated rice plants. In M. J. Constantin, R. R. Henke, K. W. Hughes and B. V. Conger, eds. Propogation Technologies and Strategies. Environmental and Experimental Botany, Permagon Press Ltd.

The homogeneous nature of a bacterial cell culture population and the cell-to-cell uniformity of gene expression throughout the fermentation have been important factors in the advancement of microbiology. These consistencies are not found in plant cell cultures to the same degree, even in cloned cell lines. It may not be possible to obtain a plant cell culture in which every cell is in a similar state of differentiation, is expressing the same genes, and has an equal capacity of divide and differentiate. Therefore, it is important to further refine existing mutation selection methodologies, to develop and test new methodologies, and seek a deeper understanding of the factors that have contributed to or hindered the successful selection of mutants in higher plants.

Most of the effort on mutant selection in plant cell and tissue culture has involved callus or suspension cell cultures. Although a number of other in vitro plant systems have been successfully employed in the recovery of mutations, they have not been exploited to the same degree. These systems include (a) embryo rescue (Gavazzi et al., 1975, Theor. Appl. Genet. 46: 339–345); (b) selection of protoplasts (Schieder, 1976, Molec. Gen. Genet. 149: 251–254); (c) selection of cultured embryos (Bright et al., 1979, Theor. Appl. Genet. 55: 1–4); (d) recovery of variant sectors on a whole plant through in vitro culture and regeneration (Radin and Carlson, 1978, Genet. Res. Comb. 32: 85–89); and (e) selection of aleurone with altered hormone sensitivity (Ho, 1979, Hormonal and genetic regulation of alpha-amylase synthesis in barley aleurone cells. Pages 147–157 in C. J. Leaver, ed. Genome Organization and Expression in Plants. Plenum Press, N.Y.; Ho and Shih, 1980, Plant Physiol. 66: 153–157).

2.2 Barley Aleurone Physiology

2.2.1 The Role of Gibberellic Acid

The hormones controlled expression of hydrolytic enzymes has been the subject of extensive research efforts for the last twenty years in order to determine whether the enzymes are synthesized de novo or are preformed before hormone action. Additionally, the effects of various transcription and translation inhibitors on this process have been reported. Briggs (1963, J. Inst. Brew. 69: 13–19), studying the mode of gibberellic acid ($GA_3$) action in aleurone reported that the alpha-amylase response was a result of $GA_3$ induction of de novo synthesis of the alpha-amylase molecule. $GA_3$ is a photohormone produced by the embryo-portion of the seed. Supporting evidence for the de novo synthesis of alpha-amylase came from the demonstration of $^{14}$C-phenylalanine incorporation into alpha-amylase (Varner, 1964, Plant Physiol. 39: 413-415) and from studies with p-fluorophenylalanine (pfp) and other amino acid analogs which reduced the incorporation of the radioactive natural amino acids into protein (Briggs, 1963, J. Inst. Brew. 69: 13-19).

Ho and Varner (1978, Arch. Biochem. Biophys. 187: 441-446) showed by $^{13}$C-density labeling that all alpha-amylase arising from treatment with $GA_3$ was a result of de novo synthesis, instead of the activation of an inactive precursor. Both alpha-amylase and protease begin to be synthesized and secreted between 8 and 10 hours after addition of $GA_3$ to the medium (Jacobsen and Varner, 1967, Plant Physiol. 42: 1596-1600).

Since an increased level of alpha-amylase (and some protease activity) occurred as a result of de novo synthesis, rather than activation, it was appropriate to seek the source of amino acids necessary for hydrolase production. Ultrastructural studies of aleurone cells (Jones, 1969, Planta 85: 359-375; Jones, 1969, Planta 87: 119-133) revealed the existence of a membrane-bound proteinaceous organelle, the "aleurone grains." With exposure to $GA_3$, the aleurone grain was observed to swell, mainly in the peripheral proteinaceous region (Jones, 1969, Planta 87: 119-133). Varner and Chandra (1964, Proc. Natl. Acad. Sci. U.S.A. 52: 100-106) reported an increase in the size of the aleurone free amino acid pool when the barley half-seeds (seeds from which the embryo has been removed) were incubated in the presence of $GA_3$. These two observations suggested that reserve protein in aleurone grains was hydrolyzed (accounting for swelling of the aleurone grain) to ree amino acids for their subsequent incorporation into new hydrolase protein (Jones, 1969, Planta 87: 119-133).

In characterizing the alpha-amylase response, Varner (1964, Plant Physiol. 39: 413-415) studied the effects of several metabolic inhibitors. Incubation with $10^{-3}$ M dinitrophenol (DNP) was severely inhibitory, indicating a requirement for oxidative phosphorylation. Incubation with chloramphenicol, cycloheximide, or pfp in the medium inhibited alpha-amylase activity, suggesting a requirement for protein synthesis. In addition, maximum expression of alpha-amylase in half-seeds or aleurone layers is not observed under anaerobic conditions. (Varner, 1964, Plant Physiol. 39: 413-415).

2.2.2 RNA Metabolism

Studies with actinomycin D (Act D), a transcription inhibitor, revealed that alpha-amylase production was sensitive only if the inhibitor was added to the half-seed incubation medium within the first seven- to eight-hour period of exposure to $GA_3$ (Chrispeels and Varner, 1967 Plant Physiol. 42: 1008-1016; Varner et al., 1965, J. Cell. Comp. Physiol. 66: 55-58; Varner and Chandra, 1964, Proc. Natl. Acad. Sci. U.S.A. 52: 100-106). It has been shown that a stable RNA component was synthesized in response to $GA_3$ between four and eight hours after addition of the hormone (Chrispeels and Varner, 1967, Plant Physiol. 42: 1008-1016; Goodwin and Carr, 1972, Planta 106: 1-12:). Alpha-amylase formation, they proposed, is dependent on the synthesis of this RNA component.

Another investigation into a $GA_3$ effect on RNA metabolism (Zwar and Jacobsen, 1972, Plant Physiol. 49: 1000-1006) revealed a small fraction of RNA, $GA_3$-induced mRNA, had incorporated labeled RNA precursors in response to $GA_3$ treatments at a greater rate than other RNA fractions. Moreover, alpha-amylse production and the enhancement of the $GA_3$-induced mRNA occurred at the same time. No effect was observed on the synthesis of rRNA for tRNA in response to $GA_3$-treatments (Jacobsen and Zwar, 1974, Aust. J. Plant Physiol. 1: 343-346). The production of alpha-amylase was inhibited drastically when cordycepin was added simultaneously with $GA_3$ (Ho and Varner, 1974, Proc. Natl. Acad. Sci. U.S.A. 71: 4783-4686); cordycepin is thought to terminate RNA chains during RNA synthesis. Addition of cordycepin at successively later times following addition of $GA_3$ results in successively less alpha-amylase inhibition until 12 hours, when no inhibition was evident. This suggests from these results that an association of mRNA in polysomes bound to endoplasmic reticulum may account for this accumulation or stabilization of mRNA.

More recently, Higgins et al. (1976, Nature 260: 166-169) attempted to relate $GA_3$-stimulated alpha-amylase production to the level of alpha-amylase mRNA. Gibberellic acid appeared to increase the level of translatable mRNA for alpha-amylase. Furthermore, there was a positive correlation between the level of translatable mRNA and the rate of alpha-amylase synthesis in vivo in response to treatments with $GA_3$.

In summary, $GA_3$ has two effects on the production of alpha-amylase in the aleurone: (1) during the first 12 hours, $GA_3$ action results in an increase in transcription and an increase in mRNA production for alpha-amylase ($GA_3$-induced mRNA); and (2) after the first 12 hours, $GA_3$ induces more efficient translation of this mRNA; possibly by a faster initiation mechanism.

2.2.3 Alpha-Amylase Secretion in Barley Aleurone

The mode of enzyme secretion in barley aleurone tissue has presented a problem in the basic understanding of the function of these specialized cells. Presently, two different ideas are expressed in the literature. One view favors packaging the hydrolases in vesicles derived from endoplasmic reticulum and the eventual release of these enzymes at the plasmalemma (Firn, 1975, Planta 125: 227-233; Gibson and Paleg, 1976, J. Cell Sci. 22: 413-425; Locy and Kende, 1978, Planta 143: 89-99; Virgil and Ruddat, 1973, Plant Physiol. 57: 549-558). The second view favors enzyme formation on rough endoplasmic recticulum and subsequent release into the cytoplasm as a soluble enzyme (Chen and Jones, 1974, Planta 119: 193-206, and 207-220; Jones and Chen, 1976, J. Cell Sci. 20: 183-198).

2.2.4 Abscisic Acid Effects on Aleurone Physiology

The plant hormone abscisic acid (ABA) is known to prevent many of the $GA_3$ effects on aleurone hydrolase production (Ho and Varner, 1976, Plant Physiol. 57: 175-178; Mozer, 1980, Cell 20: 479-485). Generally, when ABA is added at any time after initiation of aleurone layer incubation with $GA_3$, the synthesis and secretion of alpha-amylase is prevented (Ho and Varner, 1976, Plant Physiol. 57: 175-178). This suggests that ABA is not acting at the same level of control as $GA_3$. Mozer, (1980, Cell 20: 479-485), has demonstrated that ABA does not prevent the formation of translatable mRNA for alpha-amylase even though in vivo synthesis of alpha-amylase was reduced, thus indicating that ABA may be functioning in the control of translation. A clear understanding of the interaction of ABA and GA$_3$, and the molecular mechanisms of their control of aleurone metabolism is not at hand.

In an attempt to develop new approaches to study plant hormone action in aleurone, Ho (1979, Hormonal and genetic regulation of alpha-amylase synthesis in barley aleurone cells. In: Genome Organization and Expression in Plants Ed. C. J. Leaver. Plenum Press, New York, pp. 147-157; 1980, Plant Physiol. 66: 153-157) has selected for barley mutants with altered hormone sensitivity in their aleurone layers using a solid media half-seed assay. Several classes of hormone mutants were isolated including two exhibiting a homozygous Ga$_3$-insensitivity. These mutants exhibited normal plant height and GA$_3$ uptake into the aleurone but exhibited a reduced level of alpha-amylase production and phosphatase release. These mutants and others are likely to prove useful as experimental probes in the further characterization of germination physiology as well as in the elucidation of the mechanisms of hormone action.

2.3 Alpha-Amylase Genetics

Nilan (1974, Barley (*Hordeum vulgare*). Pages 93-110 in Handbook of Genetics, R. C. King, ed. Plenum Press, New York) includes in a list of barley genes that have been located on or associated with specific chromosomes, a gene for alpha-amylase (Amy) on chromosome 6. Barley varieties differ in their alpha-amylase activity during seed germination. An association between the "I" gene that governs lateral floret fertility in barley and alpha-amylase activity has been reported (Hockett and Standridge, 1975, Relationship of agronomic and malt characteristics of isogenic traits to breeding two- and six-rowed barley. Pages 594-603 in Barley Genetics III. H. Gaul, ed. Verlag Karl Thiemig, Muchen). Hayter and Allison (1975, Breeding for high diastatic power. Pages 612-619 in Barley Genetics III. H. Gaul, ed., Verlag Karl Thiemig, Muchen) selected 23 mutants out of 18,000 seeds from an ethylmethanesulfonate (EMS)-mutagenized population that were able to germinate in the presence of an inhibitory concentration of abscisic acid. One of these 23 mutants had an increased level of total nitrogen and of alpha-amylase activity. In another experiment, they demonstrated that alpha-amylase activity could be increased by selection in segregating populations. This information indicates that alpha-amylase activity is subject to being manipulated via either hybridization or mutagenesis.

There are several reports demonstrating the presence of separate alpha-amylase isoenzymes produced by barley aleurone tissue during germination (Jacobsen et al., 1970, Plant Physiol. 451: 367-371; Momatani and Kato, 1971, Plant Cell Physiol. 12: 405-410; Roadway, 1978, Phytochemistry, 17: 385-389).

2.4 Selection for High Free Lysine Mutants

The possibility of improving protein quality by mutant selection or the "engineering" of new varieties has stimulated much research activity in recent years (Bogorad and Weil, 1977, eds. Nucleic Acids and Protein Synthesis in Plants. Plenum Press, N.Y., 4517 pp.; Miflin, 1975, in Fertilizer Use and Protein Production: Proceedings of the 11th Colloquium of the International Potash Institute, pp. 55-74; Welsh, 1979, Seed Protein Improvement in Cereals and Grain Legumes: Proceedings at a Symposium. IAEA, Vienna, 2 Vols.). Although considerable progress has been made in understanding the molecular biology of storage protein synthesis and deposition, little is known about the pathways involved in providing the required forms of reduced nitrogen for storage protein synthesis. Not only are the source and form of the nitrogen supplied to the developing endosperm unclear, but also, little is known about the factors regulating the supply of nitrogen, or of the types of regulatory constraints functioning in the pathways involved in the transformations of nitrogen within the developing endosperm.

Recent research efforts in several laboratories have demonstrated the involvement of amino acid biosynthetic pathways (present in cereal endosperm tissue) during the grain filling process (Gengenbach, et al., 1978, Crop Science 17: 472-476; Henke and Wahnbaeck, 1977, Biochem. Biophys. Res. Comm. 79: 38-45; Henke and Wahnbaeck-Spencer, 1979, PEBS Letters 99: 113-116; McConnell, 1969, Can. J. Biochem. 47: 19-23; Oaks, et al., 1979, in FAO/IAEA Symposium on Seed Improvement in Cereals and Grain Legumes, Vienna; Sodek, 1976, Phytochem. 15: 1903-1906; Sodek, 1978, Revta. Brasil. Bot. 1: 65-69; Sodek and DaSilva, 1977, Plant Physiol. 60: 602-605). The pathway for the asparate family of amino acids (lysine, methionine and theonine) has been shown to be functioning in developing cereal endosperm (FIG. 1). The synthesis of the asparate-derived amino acid appears to be limited by one or more regulatory constraints (e.g., (1) feedback inhibition of pathway enzyme activity by the end product amino acids and (2) changes in the levels of extractable enzyme protein (Henke and Wahnbaeck, 1977; Biochem. Biophys. Res. Comm. 79: 38-45; Henke and Wahnbaeck-Spencer, 1979, FEBS Letters 99: 113-116; Gengenbach, et al., 1978, Crop Science 17: 472-476). This it may be feasible to develop screens that would select for mutants with defective endoproduct regulation of key control-point enzymes in the biosynthesis of lysine, methionine and threonine in developing endosperm. Such mutants may then accumulate these essential amino acids in the free pool at levels that may significantly improve the nutritional balance of the amino acid complement of the endosperm.

Mutants that overproduce lysine in yeast (Leavitt and Ryan, 1974, J. Gen. Microbiol. 80: 311-313) and rice cells (Chaleff and Carlson, 1975, in Genetic Manipulations with Plant Materials, Ledoux, ed., Plenum Press, N.Y. and London, pp. 351-363.) have been reported to exhibit an increase in protein-bound lysine as well. Madison, et al, (1979, Plant Physiol. (Suppl.) 63: 26) recently presented evidence indicating that methionine supplied to developing soybean cotyledons increased cotyledon dry weight by 27%, and the methionine content of the protein by 21% (by decreasing the ratio of 7S to 11S storage protein). These results indicate that the supply of free methionine drastically affects cotyledon development. Also, these results suggest that the supply of methionine may be limiting. An important precedent in this regard has recently been reported by Hibberd and Green (personal communication). They reported the regeneration of a fertile maize plant from a callus line resistant to lysine plus threonine. Subsequent genetic and biochemical analyses indicated that the lysine and threonine-resistant phenotype was due to a single dominant gene and that free threonine accummulated in the endosperm at a level approximately 100× the wild type. It is feasible that the lysine and threonine selection pressure has selected for a mutation in one of the pathway's controls which normally limit the synthesis of the end product amino acid threonine. Hibberd et al. (1980, Planta 148: 183–187) did find a reduced level of sensitivity to lysine by beta-asparate kinase presumably resulting in the increase in the lysine free pool observed in a different maize cell line that was also resistant to lysine plus threonine. The rationale for the selection of feedback regulatory mutants by a lysine and threonine selection pressure has be reported previously. (Green and Phillips, 1974, Corp Sci. 14: 827–830; Henke, et al., 1974, Planta 116: 333–345; Henke and Wilson, 1974, Planta 121: 155–156; Singh and Widholm, 1975, Crop Sci. 15: 79–81).

Our current understanding of the biosynthesis of lysine, methionine, and threonine in developing cereal endosperm could offer new potentials for selecting an improved nutritional balance of these amino acids in the seed. Amino acid analogs or specific combinations of naturally occurring amino acids have been employed to select for mutants that are defective in their endproduct control, and subsequently overproduce the amino acids that had been subject to that control. Plant cells in culture have been selected for resistance to different amino acid analogs, including the lysine analog Aec and have been shown to accumulate the antagonistic naturally occurring amino acid at levels greater (commonly tenfold or more) than in wild types (Widholm, 1972, Biochem. Biophys. Acta 261: 52–58; Widholm, 1972, Biochim. Biophys. Acta 279: 48–57; Palmer and Widholm, 1975, Plant Physiol. 56: 233–238; Widholm, 1976, Can. J. Bot. 54: 1523–1529; Carlson, 1973, Science 180: 1366–1368; Hibberd, et al., 1980, Planta 148: 183–187). Similar mutation screens have been conducted on mutagenized populations of germinating seeds (Brock, et al., 1973, in Nuclear Techniques for Seed Protein Improvement, Proc. of Res. Coordination Meeting, FAO/IAEA, Neurenberg; Green and Phillips, 1974, Crop Sci. 14: 827–830; Singh and Widholm, 1975, Crop Sci. 15: 79–81). Recently, Bright et al. (1979, Plant Physiol. 63: 586–588) reported the selection of a barley plant resistant to Aec and that the resistance trait was inherited as a single recessive nuclear gene. They reported that the Aec-resistance was likely due to a reduced capacity to transport Aec (Bright, et al., 1979, Theor. Appl. Genet. 55: 1–4). There are also several examples of microbes that are resistant to Aec and "overproduce" lysine (Sano and Shiio, 1970, J. Gen. Appl. Microbiol. 16: 373–391; Haidaras and Bhattacharjee, 1978, J. Ferment. Thechnol. 56: 189–192.; Takenouchi, 1979, Agric. Biol. Chem. 43: 727–734).

The inventor's laboratory has investigated the effects of Aec on barley growth and aleurone metabolism. He has shown that Aec is functioning as a lysine antagonist in the aleurone and inhibits the expression of half-seed alpha-amylase activity most likely by being incorporated in place of lysine into the newly synthesized alpha-amylase molecule. Aec does not inhibit the activity of isolated alpha-amylase. This Aec inhibition of alpha-amylase expression can be prevented when the half-seeds are incubated in the presence of lysine. It therefore seems feasible that one type of mutation that could result in aleurone/Aec-insensitivity would be a mutation resulting in significantly higher levels of lysine available for alpha-amylase synthesis. Higher levels of half-seed lysine could conceivably out compete Aec for incorporation into alpha-amylase. [The amino acid composition of barley aleurone alpha-amylase indicates 22 lysine residues per molecule (Rodaway, 1978, Phytochem. 17: 385–389)]. It is recognized that other types of mutations could confer aleurone insensitivity to the lysine analog. These mutants are of interest to us and are considered below.

Higher levels of lysine available for alpha-amylase synthesis could arise from mutations causing (1) the loss of a regulatory control in lysine synthesis; (2) changes in the level of lysine biosynthetic enzymes; and (3) changes in the rate of lysine catabolism. The gene products from these 3 types of mutations would be expressed during grain filling with the result being higher levels of lysine in the dormant seed. A mutation that resulted in approximately a 30-fold increase in free lysine would likely confer resistance to lysine analogs in the aleurone. A 30-fold increase in the free endosperm lysine would eliminate the total (free plus bound) lysine deficiency that exists in barley. The fact that free endosperm lysine in cereals only amounts to a few percent (Mertz, 1976, in Genetic Improvement of Seed Proteins, Natl. Acad. Sci., pp. 57–70) of the total in the seed may have contributed to the limited interest in research directed toward improving lysine contend in cereals by modification of the free pool component. Those selecting for "amino acid overproducers" in tissue culture systems have proposed improving the balance of amino acids in crop plants by increasing free pool levels (Chalett and Carlson, 1975, in Genetic Manipulations with Plant Materials, Ledoux, ed., Plenum Press, N.Y. and London, pp. 351–363; Widholm, 1976, Can. J. Bot. 54: 1523–1529; Bright, et al, 1979, Theor. Appl. Genet. 55: 1–4; Hibberd, et al., 1980, Planta 148: 183–187). However, actually selecting for "amino acid overproducers" in the seed itself offers the advantage of having the mutant phenotype expressed in the target tissue.

The case histories of the "high-lysine" cereals reported by Mertz (1976, in Genetic Improvement of Seed Proteins, Natl. Acad. Sci., pp. 57–70) demonstrate that far reaching metabolic changes in grain filling are associated with the known high-lysine. Included in this high-lysine syndrome are characteristics such as soft endosperm and reduced yield that have hampered the use of the high-lysine cereals. Since the biosynthetic pathway for lysine is functioning in developing cereal endosperm and is subject to one or more types of regulatory constraints it seems reasonable to expect to obtain mutants that "overproduce" and accumulate free lysine in the seed endosperm. The modification of free amino acid pools through mutation selection is an alternate approach to improving the essential amino acid balance in cereal endosperm. These types of mutations may circumvent the deleterious traits associated with the known high-lysine genes and may not be as costly bioenergetically (Mertz, 1976, in Genetic Improvement of Seed Proteins, Natl. Acad. Sci., pp. 57–70; Bhatia and Rabson, 1976, Science 194: 1418–1419; Mitra et al, Mitra, et. al., 1979, Cereal Chem. 56: 249–252). The proposed research will contribute to the evaluation of this novel approach to improving cereal quality.

2.5. Use of Bioactive Agents as Selection Pressures

The use of antibiotics and other bioactive agents for the selection of resistant mutants has been widely employed in bacterial and fungal systems. Drug-resistant mutants have contributed to the understanding of basic metabolic processes in addition to the understanding of the mode of drug action (Corcoran and Hahn, 1975, Antibiotics III. Springer Verlag, New York; Vazquez, 1974, FEBS Lett. 49(Suppl.): 563–584). Drug-resistant mutants have been successfully isolated in cultured mammalian cells as well (Thompson and Baker, 1975, Methods in Cell Biology, pp. 209–281).

The selection of drug-resistance mutants in cultured plant cells has been reported (for reviews, see Maliga, 1978, Pages 381–391 in Frontiers of Plant Tissue Culture. ed. T. A. Thorpe. Intl. Assoc. Pl. Tissue Cult., Calgary; Maliga, 1980, Intl. Review Cytol. Suppl. 11A: 225–250; Widholm, 1977. Pages 112–122 in Proceedings in Life Sciences: Plant Tissue Culture and Its Biotechnological Application, W. Barz, E. Reinhard and M. H. Zenk, eds. Springer-Verlag, Berlin; Widholm, 1978, Pages 112–122 in Propagation of Higher Plants Through Tissue Culture, K. W. Hughes, R. Henke, and M. Constantin, eds. Technical Information Center, USDOE, Tennessee). Cycloheximide, erythromycin, kanamycin and streptomycin are thought to be inhibitors of protein synthesis. Cycloheximide is thought to specifically inhibit eukaryotic protein synthesis while the others inhibit prokaryotic or organelle protein synthesis (Vazquez, 1974, FEBS Lett. 49(suppl.): 563–584). These protein synthesis inhibitors are likely to yield both nuclear and cytoplasmic mutations. Tobacco cells resistant to kanamycin and streptomycin have been obtained (Dix et al., Molec. Gen. Genet. 157: 285–290; Maliga et al., 1973, Nature 224: 29–30; Umiel and Goldner, 1976, Protoplasma 89: 83–89). This streptomycin-resistant trait was subsequently shown to be inherited in a uniparental, non-Mendelian fashion (Maliga et al., 1975, Intl. Rev. Cytol. Suppl. 11A: 225–250). Yurina et al. (1978, Theor. Appl. Genet. 52: 125–128) have recently shown that there was a change in a chloroplast ribosomal protein in one of the streptomycin-resistant tobacco mutants. Actinomycin D is thought to inhibit transcription and has been shown to inhibit the formation of alpha-amylase mRNA in barley aleurone (discussed in Section 2.2.2). Tunicamycin has been reported to inhibit the aleurone expression of alpha-amylase in barley (Schwaiger and Tanner, 1979, Eur. J. Biochem. 102: 375–381). The authors suggest that tunicamycin was inhibiting glycosylation of alpha-amylase, a reaction important for secretion of proteins.

2.6 Alpha-Amylase Assays

A number of investigators interested in the quality of milled flour and grain as well as the ability to identify the early sprouting seeds, have used alpha-amylase assays on whole grain, milled flour, and ground malt. These methods utilize starch gel diffusion assays, colorimetric assays (e.g., dye binding capacity of alpha-amylase), spectrophotometric assays, as well as gel electrophoresis (Campbell, 1980, Amer. Assoc. Cereal Chem. 24(2): 46–49; Cuvellier, et al., 1979, Brewer's Dig.; Eswaran and Nga, 1978, J. Appl. Bacteriol. 45: 287–289; Fossum and Whitaker, 1974, J. Nutr. 104: 930–936; Hejgaard and Gibbons, 1979, Carlsberg Res. Commun. 44: 21–25; Hejgaard et al., 1979, Hereditas 90: 145–147.) Ho et al. (Ho and Shih, 1980, Plant Physiol. 66: 153–157) use a half seed diffusion assay for alpha-amaylase on agar plates to screen for barley mutants with altered aleurone sensitivity to gibberellic acid or abscisic acid. However, according to the publication this screening method does not impose a selection pressure on either mutant or wild type.

The Ho et al. method involves dissecting mutagenized $M_2$ barley seeds into embryo and endosperm halves. The embryo halves were stored while the corresponding endosperm half is placed cut side down on agar containing soluble potato starch and various combinations of $GA_3$ and ABA. After incubation, the agar plates are flooded with $I_2KI$ solution (e.g., 50 mg $I_2$ plus 100 mg KI/ml distilled water). Half seeds capable of producing alpha-amylase produce transparent halos around the seed owing to the digestion of starch by alpha-amylase. These assays were performed in the varying concentrations of $GA_3$ and ABA at two different temperatures (16° C. and 28° C.).

Using this starch diffusion assay the present inventor has demonstrated that the functional alpha-amylase activity of barley half-seeds is inhibited by the lysine analog S-2-aminoethylcysteine (Aec), and that this inhibition is prevented by the addition of an exogenous supply of lysine (Henke, 1979, Plant Physiol; 63:36). Data suggests that the protein synthesis machinery is not inhibited by Aec (i.e., no apparent reduction in rate) but incorporates Aec in the place of lysine in synthesizing new protein, likely rendering these proteins damaged. However, this system has not been applied for selecting Aec-resistant mutants.

3. SUMMARY OF THE INVENTION 3.1 Brief Description of the Invention

The present invention involves a selection methodology that may conveniently and reproducibly isolate different types of mutants expressed in wheat, barley, and other cereals. The method of the invention takes advantage of the central role of alpha-amylase in seed germination. More specifically, during germination production this enzyme constitutes 60–65% of total protein synthesized. Because such as vast portion of total cell metabolism is directed to, and, consequently, reflected in alpha-amylase synthesis, this enzyme enables observation of the effect of a wide variety of biochemical mutations in a single assay. This system, in effect, magnifies the effects of mutations while at the same time allows rapid screening of a large number of individuals.

Rapid visual screening of the aleurone-gibberellic acid ($GA_3$) induced expression of alpha-amylase activity is carried out with embryo-less half-seeds under various selection pressures that normally inhibit aleurone synthesis and release of a functional alpha-amylase. Briefly, the half-seed is screened in the following manner: Embryo-less half-seeds from $M_2$ populations obtained from mutagenized [gamma, neutron, or ethylmethanesulfonate (EMS)] populations of cereal seeds are incubated in a microtiter culture plate in the presence or absence of $GA_3$, with $CaCl_2$, with soluble potato starch (SPS) or other substrate (synthetic or natural), and an appropriate selective agent. During the incubation period the aleurone tissue in the insensitive half-seeds will synthesize alpha-amylase, which will be released from the aleurone to the incubation medium and act on the substrate. The degree of hydrolysis by alpha-amylase is then measured. When the substrate utlized is SPS, staining with $I_2KI$ may be employed; a blue-black color indicates the presence of starch while a clear light-yellow color indicates the absence of starch. If synthetic substrates are utilized then the appropriate colorimetric assays well known in the art may be employed.

Appropriate incubation conditions allow complete hydrolysis of SPS (clear light yellow color) in the absence of the selection pressure and little or no SPS hydrolysis in the presence of the selective agent (blue-black color) when applied to non-mutant seed. The sharp visual contrast in color enables the convenient detection of the rare half-seed that has produced sufficient levels of alpha-amylase to totally hydrolyze the SPS even in the presence of the selection agent. The embryo corresponding to that half-seed can then be recovered and grown to maturity; the resulting progeny are then tested for the segregation of the altered aleurone phenotype. When synthetic substrates are utilized, similar sharp visual contrasts in color may be obtained as well.

3.2 General Approach and Rationale

The general approach has been to develop a selection methodology that allows rapid visual screening for different types of biochemical mutants expressed in cereal seeds. The method developed exploits the well-characterized phenomenon of the $GA_3$-induced synthesis and secretion of alpha-amylase in the aleurone tissue of cereal half-seeds. Screening may be carried out by visually detecting the level of alpha-amylase activity expressed in an embryo-less cereal half-seeds under various selection pressures that normally inhibit aleurone synthesis and release of a functional alpha-amylase.

Although a complete understanding of $GA_3$ action at the molecular level is not at hand, a great deal of evidence has accumulated indicating that the expression of alpha-amylase hydrolytic activity in the embryo-less half-seed is dependant upon the following: (a) $GA_3$ induction of transcription with the formation of a functional alpha-amylase mRNA; (b) translation of mRNA and the subsequent synthesis of new proteins, including alpha-amylase; and (c) secretion and release of alpha-amylase from the aleurone to the starchy endosperm. It is important to point out that the levels of pre-existing alpha-amylase (present in dormant aleurone) are either very low or not detectable. A more complete summary of the metabolic events occurring in aleurone tissue in response to $GA_3$ is discussed in Section 2, Background of the Invention.

One of the main objectives of the present invention is to select different types of mutations that can be recognized through alpha-amylase expression in the aleurone tissue of barley, wheat or other cereal crop plants. The present invention is based upon the recognition that many conventional selection pressures that have been described in other biological systems interfere with normal aleurone physiology, and, therefore, may be adapted for use in the present invention. The general classes of mutants are those which exhibit insensitivity or resistance to a variety of selection pressures (Table 2), i.e., the aleurone tissue will exhibit "normal metabolism" in the presence or absence of selection agents, which may be applied at various temperatures in the presence or absence of phytohormones including gibberellic acid or abscissic acid.

Several types of selection pressures can be employed to isolate different types of mutants expressed in the aleurone tissue (Table 2). Selection pressures that affect the hormone induction, transcription, translation, and secretion processes involved in the production and release of normal levels of functional alpha-amylase may be used to select mutants that are resistant to the inhibitor.

TABLE 2

SELECTIVE PRESSURES THAT MAY BE EMPLOYED IN THE BARLEY HALF SEED MUTATION SELECTION SYSTEM

| Mutant Class | Selection Pressures* |
|---|---|
| Amino acid analog-insensitive mutants | S—2-aminoethyl-L-cysteine (Aec), p-fluorophenylalanine (Pfp), and canavanine (Can), etc. |
| Drug-insensitive mutants | Actinomycin D, cordycepin, cycloheximide, kanamycin, streptomycin, tunicamycin, etc. |
| Other antimetabolite-insensitive mutants | Dinitrophenol, Potassium bromate |
| Other mutants of and other biocides agronomic importance | Herbicides (Lasso, Atrizine, Dual, (etc.) |
| | Pathotoxins |
| | Salts |
| | Metals, (Boron, Aluminum, Zinc, Cadmium, Selenium) |
| | Environmental pollutants (sulfur dioxide, aromatic hydrocarbons) |

*Half-seeds that will exhibit alpha-amylase activity at various temperatures in the presence or absence of GA or ABA plus the selective agents. The normal or "wild type" phenotype would be opposite to the responses given below.

The following is a non-exhaustive list of selection agents which are suitable for use in the method of the present invention:

(A) Amino acid analogs, such as the phenylalanine analogs, p-fluorophenylalanine, furylalanine, cyclopentene alanine; the arginine analog, canavanine; and the lysine analogs, S-2-aminoethylcysteine, hydroxylysine, n-epsilon-methyllysine, 4-oxylysine, 3-aminomethylcyclohexaneglycine; methionine analogs, ethionine, methionine sulfoximide; tryptophan analogs, methyltryptophan, fluorotryptophan, azatryptophan; the tyrosine analog, 3-aminotyrosine; and the proline analogs, hydroxyproline, azetidine-2-carboxylic acid.

Aleurone insensitivity to an amino acid analog may arise from a variety of mutations. These would include, for example, mutations in the following classes: (a) transport mutants which have a reduced capacity to take up the analog into the aleurone and/or aleurone compartment where the analog interferes; (b) detoxification mutants which are capable of metabolizing the analog to render it non-inhibitory; (c) high free amino acid mutations which are insensitive to the analog as a result of increased levels of the free amino acid which compete with the analog at the site(s) of inhibition. Generally, the high amino acid phenotype could result from regulatory mutants that have lost their ability to limit the synthesis of the amino acid or from mutations with a reduced capacity to catabolize the amino acid; (d) tRNA mutations which exhibit minor modifications in specific tRNA or in aminoacyl-tRNA synthetases that would no longer recognize the analog but would maintain their abilty to recognize the natural amino acid; and (e) high background (preformed) alpha-amylase mutations which exhibit high levels of preformed alpha-amylase that would be present in the dormant aleurone tissue. Thus, even though the analog may inhibit the formation of functional alpha-amylase, the preformed alpha-amylase would be recognized by assay. Of all of the above-noted types of mutants, those which overproduce amino acids are desired to be isolated by the methods of the present invention. In particular, increases in the levels of the essential amino acids in mutants obtained through analog selections would be of significant agronomic value.

Barley mutants which produce high levels of phenylalanine have an altered phenolic acid metabolism and as a result an increased phenolic acid content. This may improve the brewing or malting quality of the barley, giving beer an improved flavor. The increased phenolic content may also increase resistance to bacterial contamination during fermentation. Finally, an increase in seed phenolic content may result in an increased resistance to pathogens.

Canavanine is an analog for arginine and other diverse amino acid pathways. Canavanine insensitive mutants tend to demonstrate an increased efficiency to reduce nitrogen in grain.

High levels of free proline have very commonly been associated with plant tissues that have suffered from some type of osmotic stress such as drought, freezing, or salt stress. It is not clear whether a high proline level are a result of a deleterious response resulting from the stress or whether proline accummulation confers some adaptive value for overcoming the stress. The isolation of mutants exhibiting high levels of free proline will help elucidate the role of proline in osmotic stress. Such mutation may confer an increased capacity for osmotic tolerance.

Amino acid analogs have been used as selection pressures in plant cell culture. Now that some of the important biochemical pathways of the seed have been elucidated (such as the aspartate pathway) it is feasible to apply these selection pressures to the half seed assay system.

The rationale for developing mutants which overproduce lysine is different from that for other amino acids. As noted in Section 2.4, cereal grains are known to be deficient in lysine as compared to other amino acids. However, pathways for biosynthesis of amino acids other than the aspartate family are less well known in seed tissue. Furthermore, the effect of any given analog on plant metabolism (e.g., protein synthesis) should be examined on an individual basis since each analog may effect metabolism differently. Also, each natural amino acid, though contained in protein, may be involved in different secondary metabolic roles that affect the yield and quality of the seed differently.

(B) Bioactive agents, herbicides, biocides, and pathotoxins which may operate at any of the following levels: (a) Inhibitors of RNA synthesis. These transcription inhibitors include such agents as Actinomycin D, Cordycepin, Aureolic Acid, Chromomycin, Gliotoxin, etc. (b) Inhibitors of protein synthesis or secretion. These translation inhibitors include among others, Chloramphenicol, Cycloheximide, Erythromycin, Kanamycin, and Streptomycin. Tunicamycin inhibits the secretion of protein. (c) Antimetabolites other than amino acid analogs. Many of these antimetabolites (e.g., dinitrophenol, potassium bromide) inhibit mitochondrial action. These antimetabolites include (i) uncoupling agents such as dinitrophenol (DNP) or dicumarol, which allow electron transport to continue but prevent phosphorylation of ADP to ATP (i.e., they uncouple the energy yielding reactions from the energy conserving reactions); (ii) inhibitors of oxidative phosphorylation, such as oligomycin or rutamycin; and (iii) ionophores, such as valinomycin and gramicidin, which inhibit oxidative phosphorylation in the presence of certain monovalent cations.

(C) Any other pressures of agronomic importance such as: salt, freezing or water stress, metals (such as boron, aluminum, zinc, selenium and cadmium), and environmental pollutants (such as sulfur dioxide and aromatic hydrocarbons).

According to the method of the invention, these selection pressures may be applied in a sequential order, thus enabling the isolation of a mutant possessing two such desirable traits. For example, selection pressures such as amino acid analogs, metabolic inhibitors, or salt or water stress can be applied to seeds in the absence or presence of plant hormones at various temperatures.

Additionally, mutants may be isolated which are resistant to two or more of such selection agents, when the selection agents (pressures) are applied sequentially. For example, selection for insensitivity to two or more unrelated amino acid analogs could be used to specifically select for mutants exhibiting high levels of preformed alpha-amylase present in the seed.

A primary benefit of the method of the invention is the development of cereal mutants that overproduce the nutritionally essential amino acids (the essential amino acids for humans and non-ruminant animals are leucine, isoleucine, valine, methionine, threonine, lysine, histidine, phenylalanine, and tryptophan). Thus, cereals could be developed that accumulate the essential amino acids in the seed itself, and thereby eliminate the necessity of using microbes or organic synthesis to produce amino acids for feed supplements. Mutants which demonstrate increased phenolic acid content or mutants which are resistant to canavanine or other compounds may also be useful as noted above.

4. BRIEF DESCRIPTION OF THE DRAWING

FIG. 1 presents the pathway for the aspartate family of amino acids (lysine, methionine and threonine) which has been shown to function in developing cereal endosperm.

5. ALPHA-AMYLASE HALF-SEED SCREEN: PROTOCOL

Briefly, the alpha-amylase half-seed screen is carried out in the following manner:

(a) Barley or any other cereal crop seeds are mutagenized by gamma or neutron radiation, or ethylmethanesulfonate (EMS) or any other mutagenic agent. The seeds are then planted and allowed to self-pollinate. The second generation seeds ($M_2$ seeds) are harvested in bulk and used in the half-seed assay.

(b) These $M_2$ mutagenized seeds are dehusked, surface-sterilized and cut in half transversely. The half-seed without the embryo is used in the alpha-amylase assay. The other half of the seed, containing the embryo is saved for future analysis or for germination.

(c) The $M_2$ mutagenized half-seeds are incubated in a microtiter culture plate containing soluble potato starch (SPS) or other substrates (synthetic or natural), $CaCl_2$, $GA_3$ (unless performing the assay in the absence of $GA_3$) and the appropriate selective agent. During this incubation period, the mutants which are resistant or insensitive to the selective agent will continue to synthesize and release alpha-amylase from the aleurone. The alpha-amylase which is released into the incubation medium will hydrolyze the substrate.

(d) After incubation in SPS, an aliquot of $I_2KI$ solution is added to each well and the color reaction is scored. A resultant clear yellow color indicates that the SPS was completely hydrolyzed. The development of a deep blue-black color indicates little or no starch hydrolysis. A purple to deep yellow-bronze color indicates an intermediate level of hydrolysis. Thus, the degree of the color reaction indicates the activity of alpha-amylase.

The incubation conditions described hereafter in the Examples (i.e., concentrations of $GA_3$, $CaCl_2$, SPS, buffer, $I_2KI$, and selective agent; media volume; pH; incubation temperature and duration) allow for the complete hydrolysis of SPS (clear yellow color) in the absence of a selection pressure, and complete inhibition of SPS hydrolysis (blue-black color) in the presence of a selection pressure when applied to non-mutant or wild-type half-seeds. The sharp visual contrast in color enables the convenient detection of the rare half-seed that has produced sufficient levels of alpha-amylase to totally hydrolyse the SPS even in the presence of the selection pressure. The embryo corresponding to that half-seed can then be recovered, grown to maturity, with the resulting progeny then tested for the segregation of the altered aleurone phenotype. A detailed description of the research have accomplished on this project and the specific methods employed are given in the Examples.

6. ADVANTAGES OF THE INVENTION

The present inventor has developed a mutation selection methodology that conveniently measures the ability of an embryo-less half-seed to express alpha-amylase activity in the presence of several types of selection agents. This methodology allows rapid isolation of diverse types of mutants that should contribute to our understanding of plant biochemistry and genetics as well as provide new seed material for planting by farmers and new parental lines available for plant breeders.

The alpha-amylase half-seed selection methodology of the present invention possesses several advantages desired in a mutation selection protocol, that enable:

(a) Greater fundamental understanding of aleurone physiology and molecular biology. This understanding will aid in (a) the application of specific types of selection pressures (i.e., specific conditions for selection) and (b) in the recognition and characterization of the biochemistry of the resulting mutants.

(b) Screening on individual embryo-less half-seeds, thus allowing the recovery of the embryo for future analysis or germination.

(c) Actual screening at the enzyme level, i.e., alpha-amylase, which allows for a precise definition of a variant phenotype in terms of enzyme activity which can be determined visually, semiquantitatively or quantitatively by spectrophotometric analysis.

(d) Selection of many different mutants in the metabolic processes involved in expression of half-seed alpha-amylase activity.

(e) Screening on the tissue that will itself express the altered gene product. Altered genes expressed in nonendosperm tissue that affect aleurone function (e.g., altered $GA_3$ production by the embryo) may also be detected by the method of the invention. Altered gene products expressed in the seed may also be expressed in the whole plant (e.g., gene products involved in general intermediary metabolism, transcription, translation, amino acid metabolism, membrane metabolism, etc.).

(f) Exploitation of the well established methods for generating mutagenized populations of cereal seeds.

(g) The rapid and inexpensive screening for half-seed expression of alpha-amylase activity using a visual starch/$I_2KI$ assay which is carried out in a microtiter test plate. This allows for assaying alpha-amylase in the same medium used to incubate the half-seeds. Screening can be carried out in 100 μl per half-seed of incubation medium (10,000 seeds can be screened per liter of medium), further enabling the economic use of expensive chemicals as selective agents.

(h) Use of liquid assays which are more convenient than solid phase assays and allow simple quantitative analysis. Also, various types of commercially available accessory equipment can be used to facilitate screening, e.g., (a) auto- or semi-automatic quantitative pipetting and dilution equipment designed to be used in association with the microtiter test plates and (b) spectrophotometers for the quantitative determination of alpha-amylase activity within each well of the microtiter test plate.

7 Examples

Barley, *Hordeum vulgare*, cv. Atlas-57 was used in the following examples. Cultivated barley, a diploid (2 n=2X=14 chromosomes) self-fertilized plant, if a model organism for studies in mutagenesis (Nilan, 1974, Barley (Hordeum vulgare). Pages 93–110 in Handbook of Genetics v2 ed. R. C. King, Plenum Press, New York). Atlas-57, a cultivar released by the California Agriculture Experiment Station in 1958 (USDA Technical Bulletin 1224), has been used extensively for various research purposes. In the present example the method was performed using Bomi, and Himalaya as well as Atlas-57. The alpha-amylase control response and the response to several selection pressures were similar in all genotypes.

7.1 Mutagenesis

Atlas-57 barley seeds were treated with 400 rads tissue equivalent in air of unmoderated fission neutrons, 30,000 R of $^{60}Co$ gamma-radiation, or 0.03 M ethyl methanesulfonate (EMS) in phosphate buffer at pH 7.0 (16 hrs. aerated soaking at 22°–24° C.). A control population was not treated. These seeds were dried, planted, allowed to self-fertilize and bulk harvested. The harvested seeds, which constitute the $M_2$ seed population, were stored at 10° C. and 35% relative humidity. Results of mutagenesis on seed germination and plant morphology are described in Table 3.

TABLE 3

SEED GERMINATION AND MORPHOLOGICAL ABNORMALITIES IN VARIOUS POPULATIONS OF ATLAS-57 BARLEY

| Population (M2) | % Germination (in half-seeds) | Albino n | (%) | Yellow n | (%) | Dwarf* n | (%) |
|---|---|---|---|---|---|---|---|
| Control | 500 | 94 | 0 | — | 0 | — | — | — |
| EMS | 500 | 80 | 5 | (1.3) | 3 | (0.7) | — | — |
| Gamma | 500 | 87 | 4 | (0.9) | 2 | (0.4) | — | — |
| TOTAL | 1000 | 84 | 9 | (1.1) | 5 | (0.6) | — | — |
| Aec | 344 | 70 | 7 | (2.9) | 4 | (1.7) | 7 | (2.9) |
| PFP | 185 | 62 | 4 | (3.5) | 2 | (1.7) | 2 | (1.7) |
| CHI | 176 | 71 | 5 | (4.0) | 2 | (1.6) | 3 | (2.4) |
| TOTAL | 705 | 68 | 16 | (3.3) | 8 | (1.7) | 12 | (2.5) |

*Two dwarf types:
(1) grasslike;
(2) short stature.

7.2 Standard $M_2$ Screening Conditions

The standard conditions for screening $M_2$ half-seeds are as follows:

1. Barley seeds were acid dehusked (Briggs, 1963, J. Inst. Brew. 69: 13–19), surface-sterilized and cut transversely in half. The half-seeds without the embryo were used in the alpha-amylase screens and the embryo-containing portion of the seed was saved for possible future analysis.

2. Sterile microtiter tissue culture plates were used for screening. Each well contained one embryo-less half-seed and 100 μl of incubation media consisting of the following: $10^{-6}$ M $GA_3$, (except in the minus $GA_3$ screen); 20 mM $CaCl_2$; 20 mM potassium phosphate buffer, (pH 5.5); soluble potato starch, prepared according to Ho and Varner (1978, Arch, Biochem. Biophys. 187: 441-446), and the appropriate chemical selective agent, when used. The components of the incubation medium were filter sterilized except for the potato starch that was autoclaved.

3. Selection screens employed are listed in Table 4.

4. The culture plates were incubated for 24 hours at 24° C.

5. After incubation, 100 μl of $I_2KI$ solution (50 mg $I_2$ plus 100 mg KI/100 ml distilled $H_2O$) was added to each well.

6. The starch $I_2KI$ color reaction was scored as follows:

---
Response I clear yellow ($I_2KI$ color):
  apparent complete hydrolysis of
  the starch alpha-amylase.
II purple to deep yellow-bronze
  color: apparent intermediate
  level of starch and
  alpha-amylase activity.
III deep blue-black color: little
  or no starch hydrolysis.
---

7. The embryos from those half-seeds exhibiting the strong alpha-amylase response (I) were then planted in the greenhouse for selfing and the progeny tested for transmission of the trait.

7.3 Selective Agents Used

Selection screens employed (see Table 4) contained the selective agents at the concentration shown:
(a) minus-$GA_3$;
(b) abscisic acid (50 mM ABA);
(c) cycloheximide (CHI) (5 μg/ml CHI);
(d) p-fluorophenylalanine (10 mM Pfp);
(e) canavanine (10 mM Can);
(f) S-2-aminoethylcysteine (20 mM Aec).

These inhibitor concentrations resulted in only 1-2% of the half-seeds tested exhibiting the strongest alpha-amylase response (i.e., I-clear-yellow color).

Embryos corresponding to these mutant half-seeds (i.e., those exhibiting the positive alpha-amylase response) were recovered, grown to maturity, and allowed to self-pollinate. The resulting $M_3$ seeds were tested for segregation of the variant phenotype and thus provided the initial evidence for inheritance of a mutant trait. This $M_3$ segregation analysis has been completed for 116, 115 and 108 $M_2$ plants that exhibited aleurone insensitivity to the lysine analog 2-aminoethylcysteine (Aec) the phenylalanine analog p-fluorophenylalanine (Pfp) and the drug cycloheximide (CHI), respectively.

The Aec-insensitive phenotype segregated in the $M_3$ generation for 11 of 116 plants tested; three plants produced progeny that appeared homozygous and the other 8 produce progeny that segregated the mutant phenotype in various ratios. One of the homozygous Aec-insensitive mutants also expressed alpha-amylase activity in the absence of $GA_3$, also in a homozygous fashion, thus suggesting a mutation occured that resulted in a high level of preformed alpha-amylase.

The Pfp-insensitive phenotype segregated in the $M_3$ generation for 11 of 115 plants tested; 2 plants produced progeny that appeared homozygous and the remaining 8 produced progeny that segregated the mutant phenotype in various ratios. Here one of the homozygous Pfp-insensitive mutants also exhibited the homozygous expression of a dark pigmentation in the seed. It is rea-

TABLE 4
FREQUENCY OF THE ALPHA-AMYLASE RESPONSE IN SEVERAL $M_2$ SELECTION SCREENS

| Selection Agent* | Mutagen | No. Screened | No.** I | (%) | No.** II | (%) | No. Lethals |
|---|---|---|---|---|---|---|---|
| Minus $GA_3$ | Gamma | 9123 | 91 | (1.0) | 194 | (2.1) | — |
|  | EMS | 8552 | 160 | (1.9) | 238 | (2.8) | — |
|  | TOTAL | 17675 | 251 | (1.4) | 432 | (2.4) | — |
| $GA_3$ + | Gamma | 4800 | 72 | (1.5) | 194 | (4.0) |  |
| Abscisic Acid | EMS | 4800 | 82 | (1.7) | 175 | (3.6) |  |
| (50 mM) |  |  |  |  |  |  |  |
|  | TOTAL | 9600 | 154 | (1.6) | 369 | (3.8) |  |
| $GA_3$ + | Gamma | 7189 | 84 | (1.2) | 225 | (3.1) |  |
| Cyclohex- | EMS | 6720 | 92 | (1.4) | 258 | (3.8) |  |
| imide (5 g/ml) | TOTAL | 13909 | 176 | (1.3) | 483 | (3.5) |  |
| $GA_3$ + | Gamma | 6715 | 115 | (1.6) | 370 | (5.5) |  |
| p-fluoro- | EMS | 6857 | 70 | (1.0) | 273 | (4.0) |  |
| phenylalanine | TOTAL | 13572 | 185 | (1.3) | 643 | (4.7) | 71 |
| (10 mM) |  |  |  |  |  |  |  |
| $GA_3$ + $GA_3$ | Gamma | 6240 | 122 | (2.0) | 252 | (4.0) |  |
| + Canavanin | EMS | 6144 | 109 | (1.8) | 227 | (3.7) |  |
| (10 mM) |  |  |  |  |  |  |  |
|  | Total | 12364 | 231 | (1.9) | 479 | (3.9) | — |
| $GA_3$ + 2- | Gamma | 9826 | 137 | (1.4) | 303 | (3.1) |  |
| aminoethyl- | EMS | 9373 | 207 | (2.2) | 410 | (4.4) | — |
| cysteine |  | 19199 | 344 | (1.8) | 713 | (3.7) | 104 |
| (20 mM) |  |  |  |  |  |  |  |
|  | TOTAL | 86319 | 1341 |  |  |  |  |

*When present, $GA_3$ concentration was $10^{-6}$ M.
**I clear yellow, strong alpha-amylase activity with no apparent starch;
II purple to deep yellow/bronze, apparent intermediate level of alpha-amylase activity and starch.

sonable to expect that alterations in the regulation of aromatic amino acid biosynthesis, may be the basis of the Pfp-insensitive mutation and that a related effect on the synthesis of phenolic compounds has resulted in the increased accummulation of the dark red anthocyanin pigments The CHI-insensitive phenotype segregated in the $M_3$ generation for 7 of the 108 plants tested; 2 of the 7 segregated in a homozygous fashion while the remaining 5 segregated in various ratios.

In each of the selections described compelling evidence indicates that several different types mutants have been successfully isolated. This evidence includes: (a) the relatively low range of the mutants isolated, approximately 1 in 1,000; (b) the passage of the mutant phenotype to a subsequent generation; (c) the segregation of the mutant phenotypes in various ratio including homozygous conditions; (d) the successful employment of unrelated selection pressures, Aec, Pfp and CHI; and (e) the isolation of mutants that exhibit multiple, expected phenotypes.

While the invention has been described in connection with specific embodiments thereof, it will be understood that it is capable of further modification, and this application is intended to cover any variations, uses, or adaptions of the invention following, in general, the principles of the invention and including such departures from the present disclosure as come within known or customary practice in the art to which the invention pertains and as may be applied to the essential features hereinbefore set forth, and as fall within the scope of the appended claims.

I claim:

1. A method for isolating mutant plants of a cereal crop, comprising:
   (a) mutagenizing a population of cereal seeds to form a mutagenized population comprising mutant seeds and non-mutant seeds;
   (b) growing the mutagenized population to mature plants and allowing each mature plant to self-pollinate;
   (c) havesting the progeny seeds of the mature plants;
   (d) dissecting each harvested seed to form an embryo-less half-seed and a corresponding embryo-containing portion;
   (e) incubating each embryo-less half-seed individually in medium containing gibberellic acid and under at least one non-hormonal selection pressure which prevents embryo-less half-seeds of non-mutant seeds from producing alpha-amylase;
   (f) identifying the embryo-containing portions of mutant seeds by observing the ability of corresponding embryo-less half-seeds to produce alpha-amylase under said selection pressure; and
   (g) growing the identified embryo-containing portions of mutant seeds to product mutant plants.

2. The method of claim 1 wherein the cereal crop is selected from the group consisting of wheat and barley.

3. The method of claim 1 wherein the selection pressure is incubation in the presence of an amino acid analog.

4. The method of claim 3 wherein the selection pressure is incubation in the presence of 2-aminoethylcysteine.

5. The method of claim 3 wherein the selection pressure is incubation in the presence of p-fluorophenylalanine.

6. The method of claim 3 wherein the selection pressure is incubation in the presence of canavanine.

7. The method of claim 1 wherein the selection pressure is incubation in the presence of a transcription inhibitor.

8. The method of claim 7 wherein the selection pressure is incubation in the presence of actinomycin D.

9. The method of claim 1 wherein the selection pressure is incubation in the presence of a translation inhibitor.

10. The method of claim 9 wherein the selection pressure is incubation in the presence of cycloheximide.

11. The method of claim 1 wherein the selection pressure is incubation in the presence of an antimetabolite.

12. The method of claim 1 wherein the selection pressure is incubation in the presence of osmotic stress.

13. The method of claim 1 wherein the selection pressure is incubation in the presence of high concentrations of a metal.

14. The method of claim 1 wherein the selection pressure is incubation in the presence of an environmental pollutant.

15. The method of claim 1 wherein the selection pressure is incubation in the presence of a non-hormonal herbicide.

16. The method of claim 1 wherein the selection pressure is incubation in the presence of an insecticide.

17. The method of claim 1 wherein the selection pressure is incubation in the presence of fungicides.

18. The method of claim 1 wherein the selection pressure is incubation in the presence of a pathotoxin.

19. The method of claim 1 wherein said media contains a starch substrate susceptible to hydrolysis by said alpha-amylase.

20. The method of claim 19 wherein said starch is hydrolyzed by said alpha-amylase and the hydrolysis is detected by absence of a color reaction in the presence of iodine.

21. The method of claim 19 wherein said media is solid.

22. The method of claim 19 wherein said media is liquid.

23. The method of claim 1 wherein each embryo-less half-seed is incubated simultaneously under more than one selection pressure.

24. The method of claim 1 further comprising: (h) allowing the mutant plants to self-pollinate.

25. A method for isolating double mutant plants of a cereal crop, comprising:
   (a) mutagenizing a population of single mutant cereal seeds to form a mutagenized population comprising double mutant seeds and single mutant seeds;
   (b) growing the mutagenized population of step (a) to mature plants and allowing each mature plant to self-pollinate;
   (c) harvesting the progeny seeds of the mature plants;
   (d) dissecting each harvested seed to form an embryo-less half-seed and a corresponding embryo-containing portion;
   (e) incubating each embryo-less half-seed individually medium containing gibberellic acid and under at least one non-hormonal selection pressure which prevents embryo-less half-seeds from single mutant seeds from producing alpha-amylase;
   (f) identifying the embryo-containing portions of double mutant seeds by observing the ability of corresponding embryo-less half-seeds to produce alpha-amylase under said selection pressure; and
   (g) growing the identified embryo-containing portions of double mutant seeds to produce double mutant plants.

* * * * *

UNITED STATES PATENT AND TRADEMARK OFFICE
CERTIFICATE OF CORRECTION

PATENT NO. : 4,425,737  Page 1 of 2

DATED : January 17, 1984

INVENTOR(S) : Randolph R. Henke

It is certified that error appears in the above-identified patent and that said Letters Patent is hereby corrected as shown below:

Column 3, line 68, "sative" should read -- sativa --.

Column 4, line 29, "capacity of" should read -- capacity to --.

Column 5, line 63, "106:1-12:)" should read -- 106:1-12) --.

Column 6, line 6, "rPNA for" should read -- rRNA or --.
Column 6, line 14, "results" should read -- resulted --.

Column 7, line 61, "4517 pp." should read -- pp. 4517 --.
Column 7, line 63, "55" should read -- 53 --.

Column 8, line 24, "theonine" should read -- threonine --.
Column 8, line 34, "This" should read -- Thus --.
Column 8, line 35, "endoproduct" should read -- end product --.

Column 9, line 7, "has be" should read -- has been --.
Column 9, line 18, "endproduct" should read -- end product --.
Column 9, line 47, "Thechnol." should read -- Technol. --.

Column 10, line 20, "contend" should read -- content --.
Column 10, line 50, "associted" should read -- associated --.
Column 10, line 54, delete "al, Mi-".
Column 10, line 55, delete "tra, et.".

Column 12, line 32, "as" should read -- a --.

Column 14, line 22, "GA" should read -- $GA_3$ --.

Column 15, line 18, "are a" should read -- is a --.

Column 17, line 17, "segreta-" should read -- segrega- --.
Column 17, line 19, delete "have".

Column 18, line 19, "if" should read -- is --.

UNITED STATES PATENT AND TRADEMARK OFFICE
CERTIFICATE OF CORRECTION

PATENT NO. : 4,425,737     Page 2 of 2

DATED : January 17, 1984

INVENTOR(S) : Randolph R. Henke

It is certified that error appears in the above-identified patent and that said Letters Patent is hereby corrected as shown below:

olumn 19, line 9 of Table 4, which reads

"imide (5 g/ml) TOTAL 13909 176 (1.3) 483 (3.5)"

hould read-- imide (5 g/ml) TOTAL 13909 176 (1.3) 483 (3.5) 51 --.

olumn 21, line 41, "havesting" should read -- harvesting --.
olumn 21, line 55, "product" should read -- produce --.

Signed and Sealed this

Twenty-fourth Day of July 1984

[SEAL]

Attest:

GERALD J. MOSSINGHOFF

Attesting Officer     Commissioner of Patents and Trademarks